United States Patent
Kameo et al.

(10) Patent No.: US 9,340,472 B2
(45) Date of Patent: May 17, 2016

(54) METHOD FOR PRODUCING CONJUGATED DIENE

(71) Applicant: MITSUBISHI CHEMICAL CORPORATION, Chiyodu-ku (JP)

(72) Inventors: Hiroshi Kameo, Okayama (JP); Hidenobu Kajitani, Okayama (JP); Kazuyuki Iwakai, Okayama (JP); Hiroshi Takeo, Okayama (JP); Souichi Orita, Okayama (JP); Takeshi Takeuchi, Okayama (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 275 days.

(21) Appl. No.: 14/021,425

(22) Filed: Sep. 9, 2013

(65) Prior Publication Data

US 2014/0012057 A1    Jan. 9, 2014

Related U.S. Application Data

(63) Continuation of application No. PCT/JP2012/055866, filed on Mar. 7, 2012.

(30) Foreign Application Priority Data

Mar. 9, 2011  (JP) .................. 2011-051661
Mar. 22, 2011 (JP) .................. 2011-062710

(51) Int. Cl.
*C07C 5/48* (2006.01)
*B01J 23/882* (2006.01)

(52) U.S. Cl.
CPC .............. *C07C 5/48* (2013.01); *B01J 23/882* (2013.01); *C07C 2523/16* (2013.01); *C07C 2523/28* (2013.01); *C07C 2523/75* (2013.01); *Y02P 20/52* (2015.11)

(58) Field of Classification Search
CPC ........ C07C 5/48; C07C 11/167; C07C 11/16; C07C 2523/16; C07C 2523/28; C07C 23/75; B01J 23/882
USPC .......................................... 585/626
See application file for complete search history.

(56) References Cited

U.S. PATENT DOCUMENTS 3,919,257 A * 11/1975 Milberger ................. B01J 8/06
                                                            549/258
6,620,969 B1    9/2003 Nishimura et al.

(Continued)

FOREIGN PATENT DOCUMENTS

EP    2 363 203 A1    9/2011
JP    54-48399 A      4/1979

(Continued)

OTHER PUBLICATIONS

Combined Office Action and Search Report issued Aug. 25, 2014 in Chinese Patent Application No. 201280011904.3 (with English language translation).

(Continued)

*Primary Examiner* — In Suk Bullock
*Assistant Examiner* — Jason Chong
(74) *Attorney, Agent, or Firm* — Oblon, McClelland, Maier & Neustadt, L.L.P.

(57) ABSTRACT

Disclosed is a method for producing a conjugated diene by subjecting a monoolefin having a carbon atom number of 4 or more and an oxygen gas to an oxidative dehydrogenation reaction by using a molybdenum-containing metal oxide catalyst under heat removal with a coolant, wherein an amount of molybdenum adhered onto a cooling heat transfer surface within a reactor is kept at not more than 20 mg/m², or not only a surface roughness Ra of a cooling heat transfer surface within a reactor is not more than 3 μm, but a temperature difference between a reaction temperature and a coolant temperature is in the range of from 5 to 220° C.

8 Claims, 4 Drawing Sheets

(56) References Cited

U.S. PATENT DOCUMENTS

2008/0300414 A1 12/2008 Schliephake et al.
2009/0062496 A1 3/2009 Shaffer et al.
2012/0130137 A1 5/2012 Orita et al.

FOREIGN PATENT DOCUMENTS

| JP | 5-48319 B2 | 7/1993 |
| JP | 10-087517 | 4/1998 |
| JP | 2000-266477 A | 9/2000 |
| JP | 2003-220335 | 8/2003 |
| JP | 2003-284942 | 10/2003 |
| JP | 2006-142288 A | 6/2006 |
| JP | 2006-247452 | 9/2006 |
| JP | 2010-90082 A | 4/2010 |
| JP | 2010-149105 A | 7/2010 |
| JP | 2010-529005 A | 8/2010 |
| JP | 2011-6395 | 1/2011 |
| WO | WO 2009/029366 A1 | 3/2009 |
| WO | 2010/063655 | 6/2010 |
| WO | 2010/137595 | 12/2010 |

OTHER PUBLICATIONS

Office Action issued Feb. 10, 2015 in Japanese Patent Application No. 2012-050527 (with English language translation).
Office Action issued Feb. 10, 2015 in Japanese Patent Application No. 2012-059291 (with English language translation).
Information Offer Form issued Feb. 2, 2015 in Japanese Patent Application No. 2012-059291 (with English translation).
Combined Office Action and Search Report issued Apr. 24, 2015 in Taiwanese Patent Application No. 101107846 (with English language translation).
Office Action issued Apr. 8, 2015 in Chinese Patent Application No. 201280011904.3 (with English language translation).
Office Action issued May 21, 2015 in Singaporean Patent Application No. 2013066667.
Mostafa M. Awad, "Fouling of Heat Transfer Surfaces" Heat Transfer—Theoretical Analysis, Experimental Investigations and Industrial Systems, 2011, 40 Pages.
Decision of Refusal issued Jun. 30, 2015 in Japanese Patent Application No. 2012-059291 (with English machine translation).
Decision of Refusal issued Jul. 28, 2015 in Japanese Patent Application No. 2012-050527 (with unedited computer generated English translation).
International Search Report issued Jun. 5, 2012 in PCT/JP2012/055866 filed Mar. 7, 2012.
J Buiten, J Catalysis, 1968, vol. 10, p. 188-199.
Information Offer Form issued Jan. 6, 2015 in Japanese Patent Application No. 2012-050527 (with English language translation).
"Output object of the homepage of MITEC Co., Ltd." http://www.mitec-f.net/technique/conversion.html, Dec. 2014, 2 pages.
"Output object of the homepage of Guhring Japan Corporation" http://www.guhring.co.jp/techinfo/08.html, Dec. 2014, 2 pages.
Office Action issued Mar. 23, 2016, in Singaporean Patent Application No. 2013066667.

\* cited by examiner

—— MOLYBDENUM TRIOXIDE
○  CARBON CONTENT (COKE)

METHOD FOR PRODUCING CONJUGATED DIENE

TECHNICAL FIELD

The present invention relates to a method for producing a conjugated diene. In particular, the present invention relates to a method for producing a conjugated diene such as butadiene and the like through a catalytic oxidative dehydrogenation reaction of a monoolefin having the carbon atom number of 4 or more, such as n-butene and the like.

BACKGROUND ART

A method for producing a conjugated diene such as butadiene and the like by subjecting a monoolefin such as n-butene and the like to an oxidative dehydrogenation reaction in the presence of a catalyst is conventionally known.

This reaction proceeds according to, for example, the following reaction formula, and water is formed as a by-product.

$$C_4H_8 + \tfrac{1}{2}O_2 \rightarrow C_4H_6 + H_2O$$

As a production catalyst of butadiene through a representative oxidative dehydrogenation reaction of n-butene, there is a metal oxide catalyst containing molybdenum. For example, Patent Document 1 describes a complex metal oxide catalyst containing silica as well as at least one member of molybdenum, iron, nickel, and cobalt.

The metal oxide catalyst containing molybdenum is also used on the occasion of obtaining an unsaturated nitrile such as acrylonitrile and the like by allowing propylene to react with ammonia and oxygen by an ammoxidation method. However, Non-Patent Document 1 describes that water and a molybdenum compound react with each other to form a volatile molybdenum hydrate, and there is a concern that volatilized molybdenum deposits in a cooling pipe or the like within a reaction apparatus, thereby eroding a quality of the material. Accordingly, Patent Document 2 describes that by constituting a reaction apparatus using a material having a standard electrode potential of oxidation reaction in an aqueous solution system of −0.2 V or more and not more than 2.8 V, adhesion of the molybdenum compound can be suppressed.

BACKGROUND ART DOCUMENT

Patent Document

Patent Document 1: JP-A-2003-220335
Patent Document 2: JP-A-2006-247452

Non-Patent Document

Non-Patent Document 1: J. Buiten, *J. Catalysis,* 10, 188-199 (1968)

SUMMARY OF INVENTION

Problem that Invention is to Solve

In the above-described Patent Document 1, though a specific production method of butadiene is not described, there has become clear a phenomenon in which since the oxidative dehydrogenation reaction for producing butadiene from butene is an exothermic reaction, when butadiene is formed from butene as a raw material in the presence of a molybdenum-containing metal oxide catalyst by using a heat-exchange-type reactor (e.g., a fixed bed reactor, a fluidized bed reactor and the like) for performing the reaction while removing heat with a coolant or the like, adhesion of a carbon content (hereinafter also referred to as "coking") onto the inside of the reactor or the catalyst occurs. In particular, when coking occurs on the cooling heat transfer surface within the reactor, the heat removal effect is lowered, so that the reaction cannot be controlled. Therefore, when the coking occurs, by stopping the reaction each time and opening the reactor, the reactor must be cleaned up for the purpose of removing the carbon content adhered within the reactor. Thus, butadiene could not be produced stably over a long period of time. In addition, there is a concern that when the coking conspicuously proceeds within the reactor, the reactor is clogged, and a differential pressure before and after the reactor increases, so that the reaction cannot be controlled.

In view of the foregoing problem, the present invention has been made, and an object thereof is to provide a method for producing a conjugated diene such as butadiene and the like through a catalytic oxidative dehydrogenation reaction of a monoolefin such as n-butene and the like, wherein the operation can be stably continued, thereby producing butadiene industrially advantageously.

Means for Solving Problem

In order to solve the foregoing problem, the present inventors made extensive and intensive investigations. As a result, they presumed a mechanism in which on the occasion of producing butadiene through an oxidative dehydrogenation reaction of butene, water is formed as a by-product; however, when brought into contact with a molybdenum-containing metal oxide catalyst, a part of molybdenum as the catalyst component becomes a volatile molybdenum hydroxide, and this molybdenum hydroxide is liberated from the catalyst, adheres onto the cooling heat transfer surface within a reactor, and then deposits as a molybdenum oxide on the cooling heat transfer surface, whereby coking occurs starting from the deposited place.

On the basis of this presumption, the present inventors have found that the coking can be suppressed by reducing a concentration of the molybdenum oxide on the cooling heat transfer surface. Furthermore, they have found that the concentration of the molybdenum oxide on the cooling heat transfer surface strongly correlates with a surface roughness of the cooling heat transfer surface within the reactor or a temperature difference between a reaction temperature and a coolant temperature; and that by controlling these, the concentration of the molybdenum oxide can be reduced, and the coking can be suppressed, leading to accomplishment of the present invention.

The gist of the present invention includes the following [1] to [6].

[1]
A method for producing a conjugated diene, comprising:
feeding a raw material gas containing a monoolefin having a carbon atom number of 4 or more and a molecular oxygen-containing gas in a heat-exchange-type reactor having a molybdenum-containing metal oxide catalyst; and
performing an oxidative dehydrogenation reaction while removing reaction heat with a coolant, thereby producing a corresponding conjugated diene,
wherein an amount of molybdenum adhered onto a cooling heat transfer surface within the reactor is kept at not more than 20 mg/m².

[2]
A method for producing a conjugated diene, comprising:
feeding a raw material gas containing a monoolefin having a carbon atom number of 4 or more and a molecular oxygen-containing gas in a heat-exchange-type reactor having a molybdenum-containing metal oxide catalyst; and
performing an oxidative dehydrogenation reaction while removing reaction heat with a coolant, thereby producing a corresponding conjugated diene,
wherein a surface roughness Ra of a cooling heat transfer surface within the reactor is not more than 3 μm, and a temperature difference between a reaction temperature and a coolant temperature is in a range of from 5 to 220° C.

[3]
The method for producing a conjugated diene as described in [1] or [2] above,
wherein a material which is used for the cooling heat transfer surface is a polished or plated material.

[4]
The method for producing a conjugated diene as described in any one of [1] to [3] above,
wherein a quality of a material which is used for the cooling heat transfer surface includes a nickel alloy.

[5]
The method for producing a conjugated diene as described in any one of [1] to [4] above,
wherein the molybdenum-containing metal oxide catalyst is a complex metal oxide catalyst which further contains bismuth and cobalt.

[6]
The method for producing a conjugated diene as described in any one of [1] to [5] above,
wherein the raw material gas is at least one gas selected from the group consisting of a fraction (BBSS) containing, as a main component, n-butene (1-butene and 2-butene) obtained by separating butadiene and i-butene from a $C_4$ fraction (BB) which is formed as a by-product in naphtha cracking; a gas containing 1-butene, cis-2-butene, or tans-2-butene, each of which is obtained by dimerization of ethylene, or a mixture thereof; a butene fraction which is formed through dehydrogenation or oxidative dehydrogenation reaction of n-butane; and a gas containing a hydrocarbon having a carbon atom number of 4, which is obtained on an occasion of performing fluid catalytic cracking of a fuel oil fraction.

Effects of Invention

According to the present invention, it is possible to suppress coking of the cooling heat transfer surface within a reactor and to prevent clogging of the reactor to be caused due to coking without lowering a heat removal effect of reaction heat. Then, it can be expected to continue the oxidative dehydrogenation reaction for producing butadiene stably over a long period of time.

BRIEF DESCRIPTION OF DRAWINGS

FIG. 2A and FIG. 2B are each a diagrammatic view of a multitubular reactor (heat-exchange-type reactor) used in the Examples of the present invention, in which FIG. 2A is a plan view of a multitubular reactor, and FIG. 2B is a diagrammatic cross-sectional view of a multitubular reactor.

MODE FOR CARRYING OUT INVENTION

Figure 1:
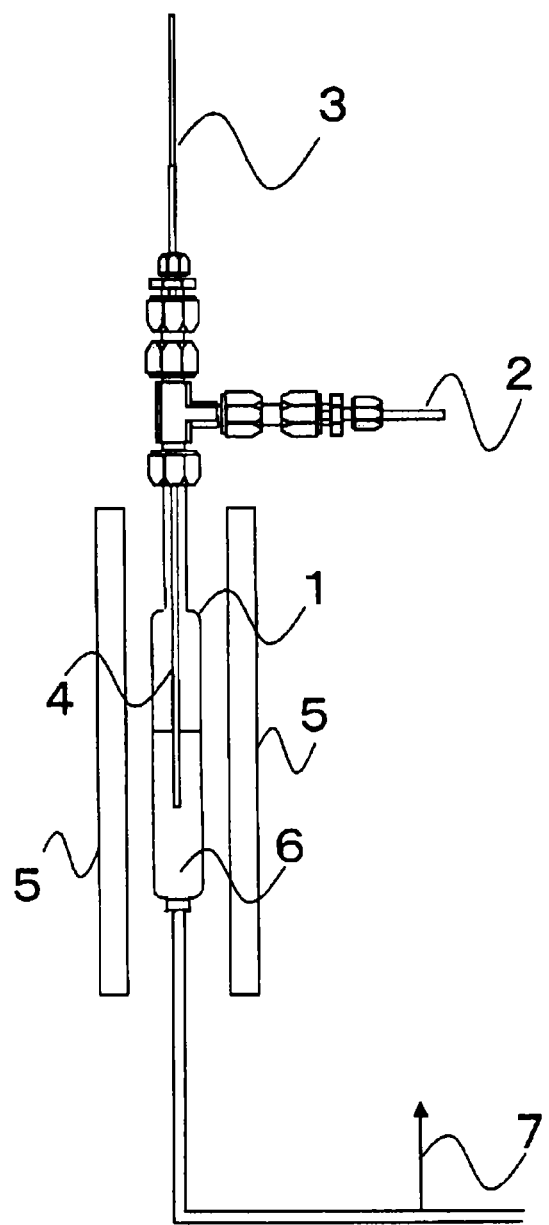
FIG. 1 is a diagrammatic view of an apparatus used in Referential Example 1 of the present invention.

Modes for carrying out a method for producing a conjugated diene of the present invention are hereunder described in detail. However, the following description is concerned with one example (representative example) of embodiments of the present invention, and the present invention is not limited to the contents thereof.

In addition, in the present description, "% by mass" and "% by weight", and "parts by mass" and "parts by weight" are synonymous with each other, respectively.

Incidentally, the present invention is described in detail by reference to the case of producing butadiene from n-butene as a representative example in the method for producing a conjugated diene of the present invention. However, the present invention is not limited to the production of butadiene from n-butene (1-butene or 2-butene) but is effectively applicable to a catalytic oxidative dehydrogenation reaction of a monoolefin having the carbon atom number of 4 or more, and preferably the carbon atom number of from 4 to 6, such as pentene, methylbutene, dimethylbutene and the like, to produce a corresponding conjugated diene.

Such a monoolefin is not necessarily used in an isolated form but can be used in a form of an arbitrary mixture, if desired.

For example, in the case where it is intended to form 1,3-butadiene from n-butene (1-butene or 2-butene), high-purity 1-butene or 2-butene can also be used as a raw material. In addition, a fraction (BBSS) containing, as a main component, n-butene (1-butene and 2-butene) obtained by separating butadiene and i-butene from a $C_4$ fraction (BB) which is formed as a by-product in naphtha cracking, or a butene fraction which is formed through dehydrogenation or oxidative dehydrogenation reaction of n-butane can also be used. The main component as referred to herein shows generally 40% by volume or more, preferably 60% by volume or more, and more preferably 70% by volume or more relative to a raw material gas.

In addition, a gas containing high-purity 1-butene, cis-2-butene, or tans-2-butene, each of which is obtained by dimerization of ethylene, or a mixture thereof, may also be used as the raw material gas. Incidentally, as for this ethylene, ethylene which is obtained by a method such as ethane dehydrogenation, ethanol dehydration, naphtha cracking, and the like can be used.

Furthermore, a gas containing a lot of a hydrocarbon having the carbon atom number of 4, which is obtained by fluid catalytic cracking in which a fuel oil fraction obtained on the occasion of distilling a crude oil in the petroleum refining plant or the like is cracked in a fluidized bed state by using a powdered solid catalyst to convert it into a low boiling point hydrocarbon (the gas will be hereunder sometimes abbreviated as "FCC-C4"), may be used as the raw material gas, as it is or a gas obtained by removing impurities such as phosphorus, arsenic and the like from FCC-C4 may also be used as the raw material gas.

In addition, arbitrary impurities may be contained in the raw material gas within the range where the effects of the present invention are not impaired. Specifically, examples of the impurities which may be contained include branched monoolefins such as isobutene and the like; saturated hydrocarbons such as propane, n-butane, i-butane, pentane and the like; olefins such as propylene, pentene and the like; dienes such as 1,2-butadiene and the like; acetylenes such as methylacetylene, vinylacetylene, ethylacetylene and the like; and the like. An amount of the impurities is generally not more than 40% by volume, preferably not more than 20% by volume, more preferably not more than 10% by volume, and especially preferably not more than 5% by volume. When this amount is excessively high, there is a tendency that the concentration of 1-butene or 2-butene as the main raw material decreases, so that the reaction becomes slow, or the yield of the desired product is lowered.

Though the form of a reactor which is used for the oxidative dehydrogenation reaction of the present invention is not particularly limited, in view of the fact that the oxidative dehydrogenation reaction is a reaction with a large heat value, a heat-exchange-type reactor which is suited for the heat removal of reaction heat is suitably used. Specifically, examples thereof include tube-type, vessel-type, or plate-type fixed bed reactors or fluidized bed reactors. Of these, fixed bed reactors are preferable, fixed bed multitubular reactors or plate-type reactors are more preferable, and fixed bed multitubular reactors are the most preferable. These reactors are those which are in general industrially used and are not particularly limited.

In general, n-butene or a mixture containing n-butene, such as BBSS and the like as described above, which serves as the raw material, is previously gasified with a vaporizer or the like before being introduced into a reactor and then fed into the reactor having a molybdenum-containing metal oxide catalyst together with a nitrogen gas, air (molecular oxygen-containing gas), and water (water vapor). Though the raw material gas, nitrogen gas, air and water (water vapor) may be fed directly through individual conduits, it is preferable that these materials are simultaneously fed in a previously uniformly mixed state into the reactor. This is because the matter that a nonuniform mixed gas forms partially a detonating gas within the reactor, or the matter that in the case of a multitubular reactor, a raw material having a different composition in every tube is fed, can be prevented from occurring.

The molecular oxygen-containing gas refers to a gas containing molecular oxygen in an amount of generally 10% by volume or more, preferably 15% by volume or more, and more preferably 20% by volume or more, and specifically, the molecular oxygen-containing gas is preferably air. Incidentally, from the viewpoint of costs necessary for industrially preparing the molecular oxygen-containing gas, the amount of molecular oxygen is generally not more than 50% by volume, preferably not more than 30% by volume, and more preferably not more than 25% by volume.

In addition, the molecular oxygen-containing gas may contain arbitrary impurities within the range where the effects of the present invention are not impaired. Specifically, examples of the impurities which may be contained include nitrogen, argon, neon, helium, CO, $CO_2$, water, and the like. In the case of nitrogen, an amount of the impurity is generally not more than 90% by volume, preferably not more than 85% by volume, and more preferably not more than 80% by volume. In the case of components other than nitrogen, an amount of the impurity is generally not more than 10% by volume, and preferably not more than 1% by volume. When this amount is excessively high, there is a tendency that it is difficult to feed oxygen necessary for the reaction.

Incidentally, in feeding the raw material gas into the reactor, the nitrogen gas and water (water vapor) may be fed together with the raw material gas. However, it is preferable to feed the nitrogen gas and water together with the molecular oxygen-containing gas and the raw material gas into the reactor from the reason that the nitrogen gas adjusts concentrations of a combustible gas such as butene and the like and oxygen such that the reaction gas does not form a detonating gas, from the reason that similar to the nitrogen gas, water (water vapor) adjusts concentrations of the combustible gas and oxygen, and from the reason that coking of the catalyst is suppressed.

In view of the fact that when the raw material gas which is fed into the reactor is mixed with the molecular oxygen-containing gas, a mixture of oxygen and a combustible gas is formed, the composition at an inlet of the reactor is controlled, for example, it is adjusted within a range of the raw material gas composition as described later, while monitoring flow rates with flow meters set in conduits for feeding the respective gases (butene and air and if desired, a nitrogen gas and water (water vapor)) such that the gas mixture does not fall within the range of explosion. Incidentally, the range of explosion as referred to herein means a range where the mixed gas of oxygen and a combustible gas has a composition such that it ignites in the presence of some ignition source. It is known that when a concentration of a combustible gas is lower than a certain value, a mixed gas does not ignite even in the presence of an ignition source, and this concentration is called a lower explosive limit.

In addition, it is known that when a concentration of a combustible gas is higher than a certain value, a mixed gas does not ignite, too even in the presence of an ignition source, and this concentration is called an upper explosive limit. Each of the values depends upon the oxygen concentration. In general, when the oxygen concentration is lower, the both values become closer to each other, and when the oxygen concentration becomes a certain value, the both coincide with each other. The oxygen concentration at that time is called a limiting oxygen concentration, and when the oxygen concentration is lower than this, the mixed gas does not ignite regardless of the concentration of the combustible gas.

There may be taken a technique in which at the time of starting the reaction of the present invention, the amounts of the molecular oxygen-containing gas such as air and the like, nitrogen and water vapor to be fed into the reactor are first adjusted such that the oxygen concentration at the inlet of the reactor is not more than the limiting oxygen concentration, feed of the combustible gas (chiefly, the raw material gas) is then started, and subsequently, the feed amounts of the combustible gas (chiefly, the raw material gas) and the molecular oxygen-containing gas such as air and the like are increased such that the concentration of the combustible gas is thicker than the upper explosive limit. There may also be taken a technique in which at the time of increasing the feed amounts of the combustible gas (chiefly, the raw material gas) and the molecular oxygen-containing gas, the feed amount of nitrogen and/or water vapor is decreased to make the feed amount of the mixed gas constant. In this way, it is possible to keep the residence time of the gas in the conduits and the reactor constant, thereby suppressing fluctuation of the pressure.

Incidentally, even when the mixed gas falls outside the range of explosion, there may be the case where when held under a certain temperature or pressure condition for a certain time, ignition is caused. The holding time at that time is called an ignition delay time. At the time of designing a circumference of the reactor, it is necessary to design it such that the residence time in the raw material conduit or formed gas conduit is not more than the ignition delay time. Since the ignition delay time depends upon the temperature, pressure or composition, it cannot be unequivocally defined. However, it is desirable that the residence time in the mixed raw material conduit is not more than 1,000 seconds, the residence time in the formed gas conduit is not more than 10 seconds, or the formed gas is cooled to not higher than 350° C. within 10 seconds.

A representative composition of the raw material gas is shown below.

<Raw Material Gas Composition> n-Butene: 50 to 100% by volume relative to a total sum of $C_4$ fraction

Total sum of $C_4$ fraction: 5 to 15% by volume $O_2$: 40 to 120% by volume relative to a total sum of $C_4$ fraction $N_2$: 500 to 1,000% by volume relative to a total sum of $C_4$ fraction $H_2O$: 90 to 900% by volume relative to a total sum of $C_4$ fraction A molybdenum-containing metal oxide catalyst as described later is present within the reactor, and n-butene reacts with oxygen on the catalyst to form butadiene and water. This oxidative dehydrogenation reaction is an exothermic reaction, and the temperature increases by the reaction. It is preferable to adjust the reaction temperature to the range of from 280 to 420° C. As for means for heat removal, the heat is removed by a coolant (for example, dibenzyltoluene, a nitrate, a nitrite and the like) or the like via a cooling heat transfer surface with which the catalyst or reaction gas within the reactor comes into contact. It is preferable to control the temperature within the reactor constant by means of heat removal.

Though the pressure of the reactor is not particularly limited, it is generally 0 MPaG or more, preferably 0.001 MPaG or more, and more preferably 0.01 MPaG or more. When this pressure value is larger, there is brought such an advantage that a large quantity of the reaction gas can be fed into the reactor. On the other hand, the pressure of the reactor is generally not more than 0.5 MPaG, preferably not more than 0.3 MPaG, and more preferably not more than 0.1 MPaG. When this pressure value is smaller, there is a tendency that the range of explosion is narrow.

Though a residence time in the reactor is not particularly limited, it is preferably 0.72 seconds or more, and more preferably 0.80 seconds or more. When this residence time value is larger, there is brought such an advantage that the conversion of the monoolefin in the raw material gas becomes high. On the other hand, the residence time in the reactor is preferably not more than 5 seconds, and more preferably not more than 4 seconds. When this residence time value is smaller, there is a tendency that the reactor becomes small.

The conjugated diene which is formed through the oxidative dehydrogenation reaction within the reactor is contained in the formed gas which is flown out from an outlet of the reactor. Though a concentration of the conjugated diene contained in the formed gas, which is corresponding to the monoolefin in the raw material gas, depends upon the concentration of the monoolefin contained in the raw material gas, it is generally from 1 to 15% by volume, preferably from 2 to 13% by volume, and more preferably from 3 to 11% by volume. When the concentration of the conjugated diene is larger, there is brought such an advantage that the recovery cost is low. When the concentration of the conjugated diene is smaller, there is brought such an advantage that when the product is compressed in a step at the later stage on and after the outlet of the reactor, a side reaction such as polymerization and the like hardly occurs. In addition, an unreacted monoolefin may also be contained in the formed gas, and its concentration is generally from 0 to 7% by volume, preferably from 0 to 4% by volume, and more preferably from 0 to 2% by volume.

In the present invention, though a by-product contained in the formed gas is not particularly limited, examples thereof include aldehydes. Though an amount thereof is not particularly limited, it is generally from 0.20 to 1.00% by weight, and preferably from 0.21 to 0.50% by weight in the formed gas.

In addition, a high boiling point by-product may also be present in the by-product contained in the formed gas. Specifically, this high boiling point by-product refers to a phthalic acid or a polycyclic aromatic compound. Specifically, examples thereof include phthalic acid, benzoic acid, anthraquinone, and the like. Though an amount thereof is not particularly limited, it is usually from 0.01 to 0.15% by weight, and preferably from 0.01 to 0.03% by weight in the formed gas.

The catalyst which is used in the present invention is a metal oxide catalyst containing molybdenum and is not particularly limited so long as it is a metal oxide catalyst containing molybdenum. A complex metal oxide catalyst further containing bismuth and cobalt in addition to molybdenum is more preferable. These catalysts themselves are a known catalyst and can be, for example, produced by a method disclosed in Patent Document 1 or the like.

Though the shape of the catalyst is not particularly limited, it can be properly changed depending upon the form of the reactor. For example, in the case of a fluidized bed reactor, the catalyst may be used upon being formed into a powder or fine particle. In addition, in the case of a fixed bed reactor, the catalyst may be shaped into an arbitrary shape by a method such as extrusion molding, tablet molding, carrying molding and the like. In addition, in order to adjust the reaction activity, an inert ball may be made present together with the catalyst in the reactor. Though the inert ball is not particularly limited so long as it is composed of a substance which is inert to the catalyst, the raw material gas, and the molecular oxygen-containing gas, for example, spheres such as silica, alumina, zirconia, and ceramic, and the like are used. The size of the inert ball is generally equal to the size of the catalyst, and its diameter is from about 2 to 10 mm when used for a fixed bed reactor and from about 10 to 300 μM when used for a fluidized bed reactor, respectively.

In the present invention, an amount of molybdenum adhered onto the cooling heat transfer surface within the reactor is kept at not more than 20 mg/m$^2$ (incidentally, the amount of molybdenum as referred to herein means an amount of molybdenum adhered onto the cooling heat transfer surface per unit area of the cooling heat transfer surface). Incidentally, the amount of molybdenum is preferably 15 mg/m$^2$, more preferably 10 mg/m$^2$, and especially preferably 5 mg/m$^2$.

Incidentally, the "cooling heat transfer surface within the reactor" is one including a heat transfer surface through which the catalyst or the reaction gas is heat exchanged with the coolant within the reactor, thereby making it possible to remove the heat generated within the reactor. For example, in the case where the heat-exchange-type reactor is a tube-type, vessel-type, or plate-type fixed bed reactor, specifically, the cooling heat transfer surface is a surface coming into contact with the charged catalyst or the reaction gas. In addition, in the case where the heat-exchange-type reactor is a fluidized bed reactor, the cooling heat transfer surface is a surface coming into contact with the catalyst in the conduit set within the reactor, through which the cooling medium flows, or a surface coming into contact with the reaction gas of a reaction gas cooler set outside the reactor.

In addition, in the present invention, it is necessary that not only a surface roughness Ra of the cooling heat transfer surface within the reactor, namely the contact surface with which the catalyst comes into contact, is not more than 3 μm, but a temperature difference between the reaction temperature and the coolant temperature is in the range of from 5 to 220° C.

In view of the fact that when the cooling heat transfer surface or temperature within the reactor is controlled/managed in this way, coking within the reactor can be suppressed, butadiene can be stably produced without causing clogging of the reactor or lowering a heat removal effect of reaction heat. As for the reasons for this, the following may be presumed.

Figure 3:
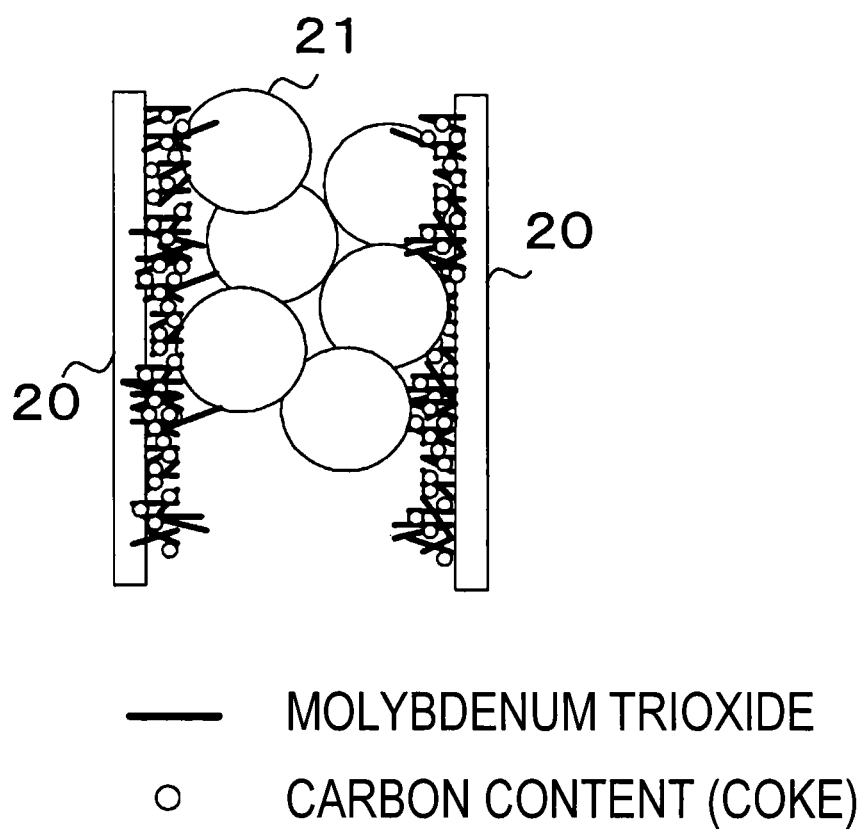
FIG. 3 is a view schematically showing a molybdenum-containing metal oxide catalyst and a state of coking of the cooling heat transfer surface.

When a monoolefin and oxygen are subjected to a vapor phase oxidative dehydrogenation reaction in the presence of a metal oxide catalyst containing molybdenum as in the present invention, a conjugated diene and water are formed. In this regard, molybdenum vaporizes as a hydrate from the catalyst due to formed water and deposits as a molybdenum oxide on the cooling heat transfer surface for the purpose of removing heat generated in the reaction. It may be considered that the deposited molybdenum oxide works like a catalyst for polymerizing conjugated dienes with each other in an atmosphere where the conjugated diene is present, whereby coking is generated such that a carbonaceous substance having a high molecular weight covers the molybdenum oxide, as shown in FIG. 3.

According to the above-described mechanism, when coking once occurs on the cooling heat transfer surface within the reactor, a coke adheres onto the surface (cooling heat transfer surface) of a heat transfer pipe coming into contact with the catalyst. Therefore, the heat transfer is impaired, the heat removal amount is lowered, and the production amount is lowered. Furthermore, in a fixed bed type reactor, circulation of the raw material becomes difficult due to clogging of the catalyst layer, so that the reaction pipe must be cleaned up by stopping the reaction and discharging the catalyst. In addition, in a fluidized bed type reactor, fluidity of the catalyst is deteriorated due to the coke, so that it is difficult to control the reaction temperature.

Figure 4:
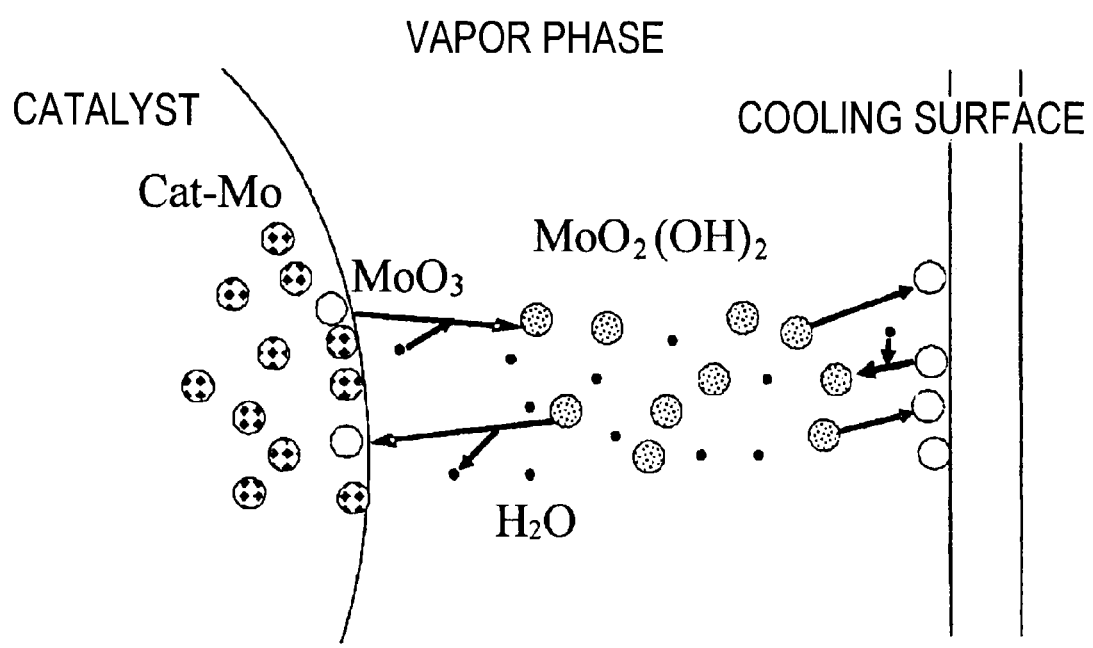
FIG. 4 is a schematic view expressing a molybdenum-containing metal oxide catalyst used for an oxidative dehydrogenation reaction and a mechanism of coking of the cooling heat transfer surface.

Then, it may be considered that when the surface roughness of the cooling transfer surface within the reactor is smaller, a space where particles of the hydrate of molybdenum vaporized from the catalyst incorporate into the surface as shown in FIG. 4 disappears, so that deposition of molybdenum is suppressed. On the basis of such a viewpoint, the surface roughness Ra may be not more than 3 μm, and it is preferably not more than 2 μm, and more preferably not more than 1.5 μm. The surface roughness Ra as referred to in the present invention is an arithmetic average roughness as defined in JIS B0601 (2001) and can be measured using a contact type roughness meter, a laser type roughness meter, or the like.

Though a method for making the surface roughness small is not particularly limited, in general, a method such as mechanical polishing with an abrasive such as a buff and the like, electrolytic polishing, plating, and the like is suitably adopted. By making a tooth of the abrasive which is used for the mechanical polishing method small, a smaller surface roughness is obtained. In addition, when electrolytic polishing is performed, a smooth surface such as a mirror surface is achieved, so that the Ra can be suitably made small. As a method for performing plating, electroplating, electroless plating, and the like are suitably adopted, and from the standpoints of corrosion of a reaction apparatus and costs, plating with nickel as a main component is suitably adopted. Electrolytic polishing and plating are a more preferred method because it is possible to smooth up to polishing marks of mechanical polishing. In addition, a material which has been previously finished to an extent of not more than 3 μm may be stuck onto the surface coming into contact with the catalyst within the reactor.

In the present invention, though a quality of the material of the cooling heat transfer surface within the reactor is not particularly limited, it preferably contains a nickel alloy. For example, stainless steels (e.g., austenite based, austenite•ferrite based, ferrite based, and martensite based stainless steels) are preferable, and stainless steels (e.g., austenite based, austenite•ferrite based, ferrite based, and martensite based stainless steels) are more preferable. Specifically, examples of the stainless steels include SUS304, SUS316, SUS329J1, SUS405, SUS403, and the like (these names are a name standardized by JIS (Japanese Industrial Standards)).

In the present invention, in addition to the matter that the above-described surface roughness Ra of the cooling heat transfer surface within the reactor is not more than 3 μm, it is necessary that a temperature difference between the reaction temperature and the coolant temperature is in the range of from 5 to 220° C. FIG. 4 is a view schematically showing vaporization of molybdenum from the molybdenum-containing metal oxide catalyst and deposition thereof onto the cooling heat transfer surface. According to the above-described mechanism, it may be considered that deposition of the molybdenum compound on the contact surface coming into contact with the catalyst is determined by a difference between a concentration of molybdenum in a vapor phase space where the catalyst is present and a vapor pressure thereof at the contact surface temperature; and that a deposition rate is determined by a difference between the molybdenum concentration in the vapor phase space and the vapor pressure of molybdenum on the cooling heat transfer surface. Namely, it may be considered that a relation represented by the following equation (I) is found to hold. In the case where the molybdenum concentration in the vapor phase is high, or the temperature of cooling heat transfer is low, and the vapor pressure of molybdenum is low, the deposition rate of molybdenum becomes high, and a large amount of molybdenum deposits on the cooling heat transfer surface, so that the coking is accelerated. On the other hand, when the molybdenum concentration in the vapor phase is low, and the vapor pressure of molybdenum on the cooling heat transfer surface is high, the vaporization of molybdenum from the cooling heat transfer surface is accelerated, so that the deposition of molybdenum onto cooling surface hardly occurs.

[Su 1]

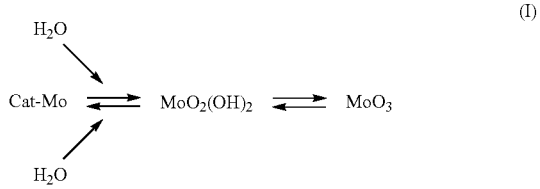

(I)

In order to prevent the deposition of molybdenum onto the cooling heat transfer surface from occurring, a difference between the temperature of the catalyst, namely the reaction temperature, and the temperature of the cooling surface may be made small.

For example, in a fixed bed type reactor, it is suitable to adopt a temperature difference of from 5 to 220° C., preferably from 15 to 150° C., and more preferably from 20 to 100°

C. When this temperature difference is too small, a large heat transfer area is necessary for the heat removal, and reversely, when it is too large, there is a tendency that a problem in a reactor structure (mechanical strength) is caused, or it is difficult to control the reaction temperature.

In addition, in the case of using a fluidized bed type reactor, as represented by a method of dipping a heat transfer pipe in a catalyst layer, it is general that the catalyst is fluidized with the raw material gas, and the outer surface of the heat transfer pipe into which a heat transfer medium is circulated is brought into contact with the catalyst, thereby removing the reaction heat.

As for the fluidized bed reactor, it is general to generate steam and to achieve the heat removal with latent heat of vaporization thereof, and a temperature of the steam is determined by a pressure of the cooling medium. Therefore, the operation is generally performed under a pressure of from 1 to 10.0 MPaG. In the case where the temperature is high (the pressure is high), there is involved such a problem that the costs of construction for satisfying pressure resistance of the apparatus become high. In addition, in the case where the temperature is low (the pressure is low), since the temperature of the generated steam is low, there is no industrial application, and the steam is discarded fruitlessly. Thus, such is not preferable from the economic standpoint. In consequence, the operation is performed under a pressure of generally from 1.0 to 10.0 MPaG, and preferably from 1.5 to 5.0 MPaG. The temperature of hot water is preferably from 180 to 310° C., and more preferably from 200 to 265° C. In consequence, a difference from the reaction temperature is preferably from 15 to 220° C., and more preferably from 30 to 200° C.

In addition, it is also effective for decreasing the molybdenum concentration in the vapor phase to decrease the concentration of water formed within the reactor. However, since water is generated following the oxidative dehydrogenation reaction, it is effective to decrease the raw material concentration, but there is involved such a problem that the production efficiency is lowered. In addition, it is a useful means to lower the concentration of water which is made coexistent in the reaction feed gas within the range where a problem is not caused regarding the explosion or coking.

As for a method for keeping the amount of molybdenum adhered onto the cooling heat transfer surface at not more than 20 mg/m$^2$ relative to the catalyst weight within the reactor, vaporization of the molybdenum component of the molybdenum-containing metal oxide catalyst may be suppressed, or deposition of vaporized molybdenum as a molybdenum oxide onto the cooling heat transfer surface may be suppressed. Means therefor can be carried out using a means for controlling the roughness of the cooling heat transfer surface or temperature difference between the reaction temperature and the coolant temperature, the steam, or the like as described above.

EXAMPLES

The present invention is more specifically described below by reference to the following Examples.

Referential Example 1

Observation of Coking of Molybdenum Trioxide (MoO$_3$)

A coking experiment of molybdenum trioxide was performed using an apparatus shown in FIG. 1. A glass-made reaction tube 1 having an inner diameter of 6 mm was charged with one gram of molybdenum trioxide 6 (manufactured by Wako Pure Chemical Industries, Ltd.). A mixed gas composed of 1,3-butadiene, oxygen, nitrogen, and water vapor and having a composition shown in Table 1 was fed in a rate of 2.0 NL/h from a raw material gas feed port 2.

The glass-made reaction tube 1 was heated to 360° C. by an electric heater 5, and the above-described mixed gas was circulated into the reaction tube for 48 hours while discharging a part of a waste gas flowing out from an outlet of the reaction tube from a discharge port 7. After elapsing 48 hours, the feed of the mixed gas was stopped, and the molybdenum trioxide 6 was taken out from the reaction tube. As a result, the molybdenum trioxide 6 was discolored black and adhered tightly. In addition, the temperature was increased under air circulation using a thermobalance, TGA/DSC1 Model, manufactured by METTLER, and a weight reduction was examined in a temperature range of from 200 to 500° C. As a result, the weight reduction was 13.6% by weight.

It is understood from this result that MoO$_3$ forms a carbonaceous compound (coke) upon contact with a gas where water and butadiene are present and causes vigorous coking.

TABLE 1

| Component name | Composition (% by volume) |
| --- | --- |
| Nitrogen | 56.5 |
| Oxygen | 5.5 |
| 1,3-Butadiene | 13.0 |
| Water vapor | 25.0 |

Referential Example 2

Preparation of Complex Metal Oxide Catalyst 54 g of ammonium p-molybdate was dissolved in 250 mL of pure water by heating at 70° C. Subsequently, 7.18 g of ferric nitrate, 31.8 g of cobalt nitrate, and 31.8 g of nickel nitrate were dissolved in 60 mL of pure water by heating at 70° C. These solutions were gradually mixed with each other while thoroughly stirring.

Subsequently, 64 g of silica was added, and the contents were thoroughly stirred. This slurry was heated at 75° C. and aged for 5 hours. Thereafter, this slurry was heated for drying and then subjected to a heat treatment in an air atmosphere at 300° C. for one hour.

A granular solid of the resulting catalyst precursor (ignition loss: 1.4% by weight) was pulverized and dispersed in a solution prepared by dissolving 40.1 g of ammonium p-molybdate in 150 mL of pure water and 10 mL of ammonia water. Subsequently, 0.85 g of borax and 0.36 g of potassium nitrate were dissolved in 40 mL of pure water under heating at 25° C., to which was then added the above-described slurry.

Subsequently, 58.1 g of bismuth subcarbonate having 0.45% of Na solid-solved therein was added, and the contents were mixed with stirring. This slurry was heated for drying at 130° C. for 12 hours. Thereafter, the resulting granular solid was subjected to tablet molding into a tablet having a diameter of 5 mm and a height of 4 mm by using a small-sized molding machine and subsequently calcined at 500° C. for 4 hours to obtain a catalyst. The catalyst as calculated from the charged raw materials was a complex oxide having the following atomic ratio.

Mo:Bi:Co:Ni:Fe:Na:B:K:Si=12:5:2.5:2.5:0.4:0.35:0.2:0.08:24

Incidentally, atomic ratios $a_1$ and $a_2$ of molybdenum on the occasion of catalyst preparation were 6.9 and 5.1, respectively.

Example 1

Figure 2A:
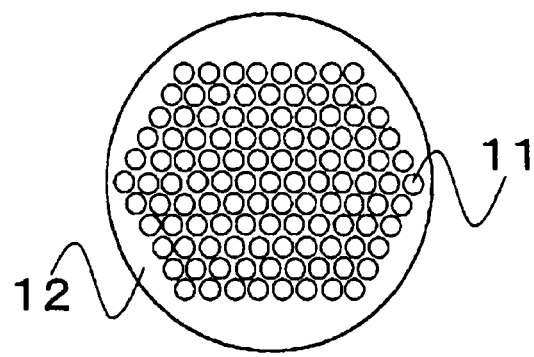
Figure 2B:
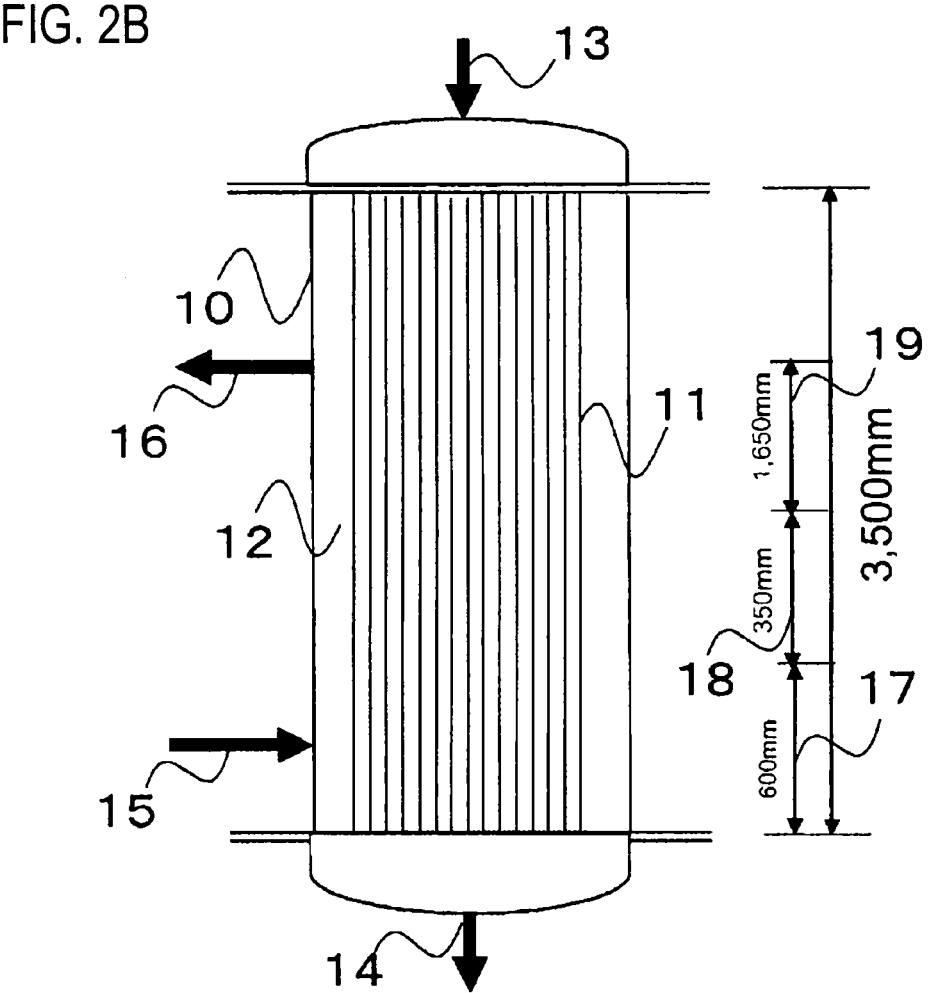

Production of Butadiene Through Oxidative Dehydrogenation Reaction of Butene The production of butadiene through an oxidative dehydrogenation reaction of butene was performed using a fixed bed multitubular reactor 10 shown in FIG. 2A and FIG. 2B. FIG. 2A is a plan view of the multitubular reactor 10, and FIG. 2B is a diagrammatic cross-sectional view of the multitubular reactor 10.

Before performing the oxidative dehydrogenation reaction of butene, five of 113 reaction tubes 11 (length: 3,500 mm, inner diameter: 27 mm, quality of material: SUS304) within the reactor 10 shown in FIG. 2A and FIG. 2B were previously extracted at random, and the inner surface of each of those five reaction tubes 11 was polished with a 180# buff (JIS H 0400). A surface roughness of the inner surface of the reaction tube was measured using a surface roughness measuring machine (Model: SJ-301, manufactured by Mitutoyo Corporation), and an average value of the surface roughness (surface roughness Ra) of the five reaction tubes was 1.3 μm.

78 mL of the catalyst obtained in Referential Example 2 and 22 mL of an inert ball were mixed and charged in a lower part of each of the thus-polished five reaction tubes 11. Furthermore, 73 mL of the catalyst and 275 mL of an inert ball were mixed and charged in an upper part thereof. Incidentally, a molybdenum concentration in the catalyst particle used for the reaction was 24.2% by weight, a silica concentration in the catalyst particle was 14.2% by weight, and a charge amount of the catalyst charged in a catalyst layer height of the reaction tube 11 of 20 cm was 63 g.

In addition, the catalyst and the inert ball were similarly charged in the other 108 reaction tubes than the five reaction tubes, which had not been polished.

Incidentally, a differential pressure of the reaction tube 11 was measured in the following manner. That is, 15 NL/min of nitrogen was circulated from the top of each of the reaction tubes, a pressure in an inlet part of the reaction tube 11 was measured, and a difference from the atmospheric pressure was defined as a differential pressure of reaction tube before starting the reaction. The results of measurement of the differential pressure are shown in Table 4.

Then, BBSS having a component composition shown in Table 2, which was discharged from an extraction separation process of butadiene from a $C_4$ fraction formed as a by-product in naphtha cracking, as a raw material gas, air, nitrogen, and water vapor were fed in flow rates of 15.7 Nm³/h, 81.7 Nm³/h, 62.5 Nm³/h, and 17.7 Nm³/h, respectively, and these were heated at 214° C. by a preheater and then fed from a raw material gas inlet 13 into the multitubular reactor 10. A coolant at a temperature of 360° C. was flown from a coolant inlet 15 into a reactor shell side 12, thereby adjusting a maximum temperature of the inside of the reactor at from 395 to 400° C.

A continuous operation of 2,000 hours was performed while extracting a butadiene-containing formed gas having a composition shown in Table 3, which was obtained from a formed gas outlet 14, and the reaction was then stopped. After stopping the reaction, a differential pressure of the reactor was measured in the same manner as that before the reaction. The results are shown in Table 4.

In addition, a wall surface deposit in the range of from the lower end of the catalyst layer of the polished five reaction tubes 11 to a portion of 200 mm upward was scraped, and an amount of the adhered molybdenum compound was measured. Furthermore, the wall surface deposit of the polished five reaction tubes 11 was analyzed by an X-ray fluorescence analyzer (Model: PW2405 Type X-ray fluorescent emission spectrometer, manufactured by Philips Inc.). In addition, a concentration of each of molybdenum and bismuth was determined from a calibration curve which had been previously prepared using a substance having an already-known concentration. The results are shown in Table 4.

Incidentally, a deposited molybdenum amount (mg) is calculated according to the following equation.

(Deposited molybdenum amount)=(Molybdenum amount in deposit)−(Molybdenum amount in adhered catalyst)=(Molybdenum amount in deposit)−(Bismuth amount in deposit)×(Molybdenum/bismuth weight ratio in catalyst)

Incidentally, a molybdenum amount (mg) in the deposit is calculated according to the following equation.

{Molybdenum amount (mg) in deposit}=(Deposit weight)×(Molybdenum concentration determined by X-ray fluorescence analysis)

A bismuth amount (mg) in the deposit is calculated in the same manner as that in the molybdenum analysis according to the following equation.

{Bismuth amount (mg) in deposit}=(Deposit weight)×(Bismuth concentration determined by X-ray fluorescence analysis)

In addition, the molybdenum/bismuth weight ratio in the catalyst is 1.10.

Then, since a surface area of the wall surface of 200 mm is $3.14 \times 0.027 \times 0.2 = 0.017$ m², the molybdenum amount (mg/m²) adhered within the reaction tube is calculated from (deposited molybdenum amount)/0.017.

TABLE 2

| Component name | Composition (% by volume) |
| --- | --- |
| n-Butane | 15.70 |
| i-butane | 4.74 |
| 1-Butene | 42.69 |
| Cis-2-butene | 13.60 |
| Trans-2-butene | 17.73 |
| Other components | 5.53 |

TABLE 3

| Component name | Composition (% by volume) |
| --- | --- |
| 1,3-Butadiene | 4.59 |
| Oxygen | 4.7 |
| Nitrogen | 69.6 |
| $H_2O$ | 16.34 |
| Other components | 4.77 |

Example 2

The same procedures as those in Example 1 were followed, except that the inner surface of each of the five reaction tubes was polished with a 400# buff (JIS H 0400) to make an average value of the surface roughness (surface roughness Ra) of the five reaction tubes to 1.1 μm. The results are shown in Table 4.

Example 3

The same procedures as those in Example 1 were followed, except that the inner surface of each of the five reaction tubes was polished with a 600# buff (JIS H 0400) to make an average value of the surface roughness (surface roughness Ra) of the five reaction tubes to 0.39 μm. The results are shown in Table 4.

Comparative Example 1

The same procedures as those in Example 1 were followed, except that an average value of the surface roughness (surface roughness Ra) of the five reaction tubes was made to 3.2 μm without polishing the inner surface of each of the five reaction tubes. The results are shown in Table 4.

7: Discharge port
10: Multitubular reactor
11: Reaction tube
12: Reactor shell side
13: Raw material gas inlet
14: Formed gas outlet
15: Coolant inlet
16: Coolant outlet
17: Inert layer
18: Lower layer of catalyst layer
19: Upper layer of catalyst layer

TABLE 4

| | Surface roughness | Temperature difference | Deposit weight | Coke amount | Amount in deposit | | Deposited Mo | Differential pressure of reaction tube | | Differential pressure | Adhered Mo |
| | Ra μm | °C. | g | g | Mo mg | Bi mg | amount mg | Before reaction mmH$_2$O | After reaction mmH$_2$O | difference mmH$_2$O | mg/m$^2$ |
|---|---|---|---|---|---|---|---|---|---|---|---|
| Example 1 | 1.3 | 39 | 0.0228 | 0.0205 | 0.043 | 0.013 | 0.029 | 158 | 165 | 7 | 1.7 |
| Example 2 | 1.1 | 39 | 0.0124 | 0.0125 | 0.028 | 0.023 | 0.003 | 156 | 162 | 6 | 0.2 |
| Example 3 | 0.39 | 39 | 0.0082 | 0.0082 | 0.027 | 0.018 | 0.007 | 155 | 162 | 7 | 0.4 |
| Comparative Example 1 | 3.2 | 39 | 0.0928 | 0.0641 | 0.924 | 0.445 | 0.434 | 156 | 168 | 12 | 25.6 |

From the results of Examples 1 to 3 and Comparative Example 1, as compared with the non-polished reaction tube, by performing the polishing with a buff to make the surface roughness Ra to not more than 3 μm and controlling the temperature difference between the reaction temperature and the coolant temperature to not more than 220° C., the deposit weight of the reaction tube becomes significantly small, and the effect for enabling clogging of the reaction tube due to coking to be avoided is exhibited. In addition, when the amount of adhered molybdenum is kept at not more than 20 mg/m$^2$, the generation of coking itself is suppressed, and an increase of the differential pressure of reaction tube is small, and hence, it is expected that butadiene can be stably produced.

While the invention has been described in detail and with reference to specific embodiments thereof, it will be apparent to one skilled in the art that various changes and modifications can be made therein without departing from the spirit and scope thereof. The present application is based on a Japanese patent application filed on Mar. 9, 2011 (Japanese Patent Application No. 2011-051661) and a Japanese patent application filed on Mar. 22, 2011 (Japanese Patent Application No. 2011-062710), the contents of which are incorporated herein by reference.

INDUSTRIAL APPLICABILITY

According to the production method of the present invention, it becomes possible to produce a conjugated diene stably over a long period of time.

EXPLANATIONS OF REFERENCE SIGNS

1: Glass-made reaction tube
2: Raw material gas feed port
3: Temperature indicator
4: Temperature indicator protective tube
5: Electric heater
6: Molybdenum trioxide 20: Cooling heat transfer surface within reactor
21: Molybdenum-containing metal oxide catalyst

The invention claimed is:

1. A method for producing a conjugated diene, comprising:
feeding a raw material gas comprising a monoolefin having a carbon atom number of 4 or more and a molecular oxygen-containing gas in a heat-exchange-type reactor having a molybdenum-containing metal oxide catalyst; and
performing an oxidative dehydrogenation reaction while removing reaction heat with a coolant, thereby producing a corresponding conjugated diene,
wherein an amount of molybdenum adhered onto a cooling heat transfer surface within the reactor is kept at not more than 20 mg/m$^2$, and
wherein a surface roughness Ra of a cooling heat transfer surface within the reactor is not more than 3 μm, and a temperature difference between a reaction temperature and a coolant temperature is in a range from 5 to 220° C.

2. The method according to claim 1, wherein a material which is used for the cooling heat transfer surface is a polished or plated material.

3. The method according to claim 1, wherein a material for the cooling heat transfer surface comprises a nickel alloy.

4. The method according to claim 1, wherein the molybdenum-containing metal oxide catalyst is a complex metal oxide catalyst which further comprises bismuth and cobalt.

5. The method according to claim 1, wherein the raw material gas is at least one gas selected from the group consisting of (i) a fraction comprising 1-butene, 2-butene, or a mixture thereof obtained from a C$_4$ fraction produced by a naphtha cracking; (ii) a gas comprising 1-butene, cis-2-butene, or trans-2-butene, or a mixture thereof, obtained by dimerization of ethylene; (iii) a butene fraction which is formed through dehydrogenation or oxidative dehydrogenation reaction of n-butane; and (iv) a gas comprising a hydrocarbon having a carbon atom number of 4, which is obtained from a fluid catalytic cracking of a fuel oil fraction.

6. The method according to claim 1, wherein a pressure of the reactor is from 0 MPaG to 0.5 MPaG.

7. The method according to claim 1, wherein a surface roughness Ra of a cooling heat transfer surface within the reactor is not more than 1.5 μm, and a temperature difference between a reaction temperature and a coolant temperature is from 20 to 100° C.

8. The method according to claim 1, wherein the coolant is at least one selected from the group consisting of dibenzyl-toluene, a nitrate, and a nitrite.

* * * * *